US011324585B2

(12) United States Patent
Algawi et al.

(10) Patent No.: US 11,324,585 B2
(45) Date of Patent: May 10, 2022

(54) METHOD FOR PRODUCING SHELL AND FOAM FILLER FOR A BREAST IMPLANT

(71) Applicant: Biosense Webster (Israel) Ltd., Yokneam (IL)

(72) Inventors: Yehuda Algawi, Binyamina (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 492 days.

(21) Appl. No.: 16/159,414

(22) Filed: Oct. 12, 2018

(65) Prior Publication Data

US 2020/0113671 A1 Apr. 16, 2020

(51) Int. Cl.
| | |
|---|---|
| *A61F 2/12* | (2006.01) |
| *A61L 27/56* | (2006.01) |
| *B29C 41/04* | (2006.01) |
| *B29C 67/20* | (2006.01) |
| *B29L 31/00* | (2006.01) |
| *A61F 2/00* | (2006.01) |
| *A61L 27/18* | (2006.01) |
| *B29K 83/00* | (2006.01) |

(52) U.S. Cl.
CPC .............. *A61F 2/12* (2013.01); *A61F 2/0077* (2013.01); *A61L 27/56* (2013.01); *B29C 41/04* (2013.01); *A61L 27/18* (2013.01); *A61L 2430/04* (2013.01); *B29C 67/202* (2013.01); *B29K 2083/005* (2013.01); *B29L 2031/7532* (2013.01)

(58) Field of Classification Search
CPC ...... A61F 2/12; A61F 2/0077; A61F 2240/00; A61F 2240/004; A61L 27/56; A61L 27/18; A61L 2430/04; B29C 67/202; B29K 2083/005; B29L 2031/7532
See application file for complete search history.

(56) References Cited

U.S. PATENT DOCUMENTS

| | | | |
|---|---|---|---|
| 5,674,285 A | 10/1997 | Quaid | |
| 5,865,237 A * | 2/1999 | Schorghuber | ......... B22F 3/1125 164/79 |
| 6,099,565 A | 8/2000 | Sakura, Jr. | |
| 7,517,923 B2 * | 4/2009 | Yoneyama | .............. C08L 31/04 524/10 |

(Continued)

FOREIGN PATENT DOCUMENTS

| | | |
|---|---|---|
| EP | 3556321 A1 | 10/2019 |
| EP | 3572040 A1 | 11/2019 |

(Continued)

OTHER PUBLICATIONS

International Application No. PCT/IB2019/058631—International Search Report dated Jan. 24, 2020.

*Primary Examiner* — Jacob T Minskey
*Assistant Examiner* — Caroline Beha
(74) *Attorney, Agent, or Firm* — Eugene L. Szczecina, Jr.

(57) ABSTRACT

A method for manufacturing a breast implant includes producing a silicone shell of the breast implant by rotating a mold containing a silicone material to evenly spread the silicone material over an inner surface of the mold. Subsequently, an elastic filler material including silicone foam is formed in the shell by (i) injecting into the mold a mixture comprising silicone gel and gas bubbles and (ii) rotating the mold to homogenize the mixture.

5 Claims, 2 Drawing Sheets

(56) References Cited

U.S. PATENT DOCUMENTS

| | | | |
|---|---|---|---|
| 8,001,974 B2* | 8/2011 | Makower | A61B 90/98 128/898 |
| 2003/0018387 A1* | 1/2003 | Schuessler | A61B 17/12099 623/8 |
| 2005/0184419 A1* | 8/2005 | Laws | B29C 41/22 264/45.7 |
| 2006/0264399 A1 | 11/2006 | Lim et al. | |
| 2008/0226715 A1* | 9/2008 | Cha | A61P 25/00 424/468 |
| 2009/0030515 A1 | 1/2009 | Schuessler et al. | |
| 2009/0210056 A1* | 8/2009 | Forsell | A61F 2/12 623/8 |
| 2010/0074934 A1 | 3/2010 | Hunter | |
| 2011/0270391 A1 | 11/2011 | Chitre et al. | |
| 2012/0303118 A1 | 11/2012 | DeBoer et al. | |
| 2013/0289529 A1 | 10/2013 | Caira et al. | |

FOREIGN PATENT DOCUMENTS

| | | | |
|---|---|---|---|
| WO | 2009113745 A1 | 9/2009 | |
| WO | 2016108228 A1 | 7/2016 | |

* cited by examiner

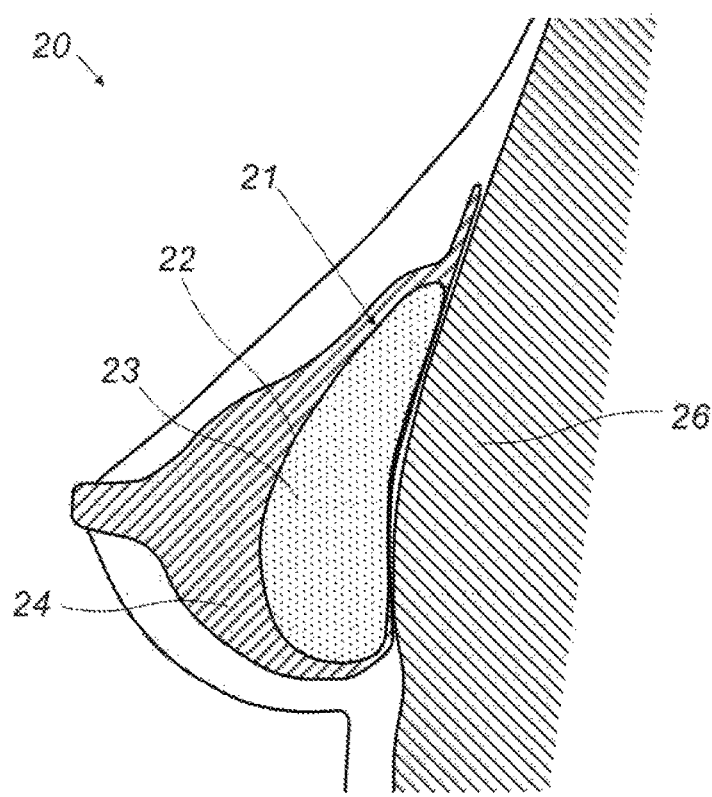
FIG. 1
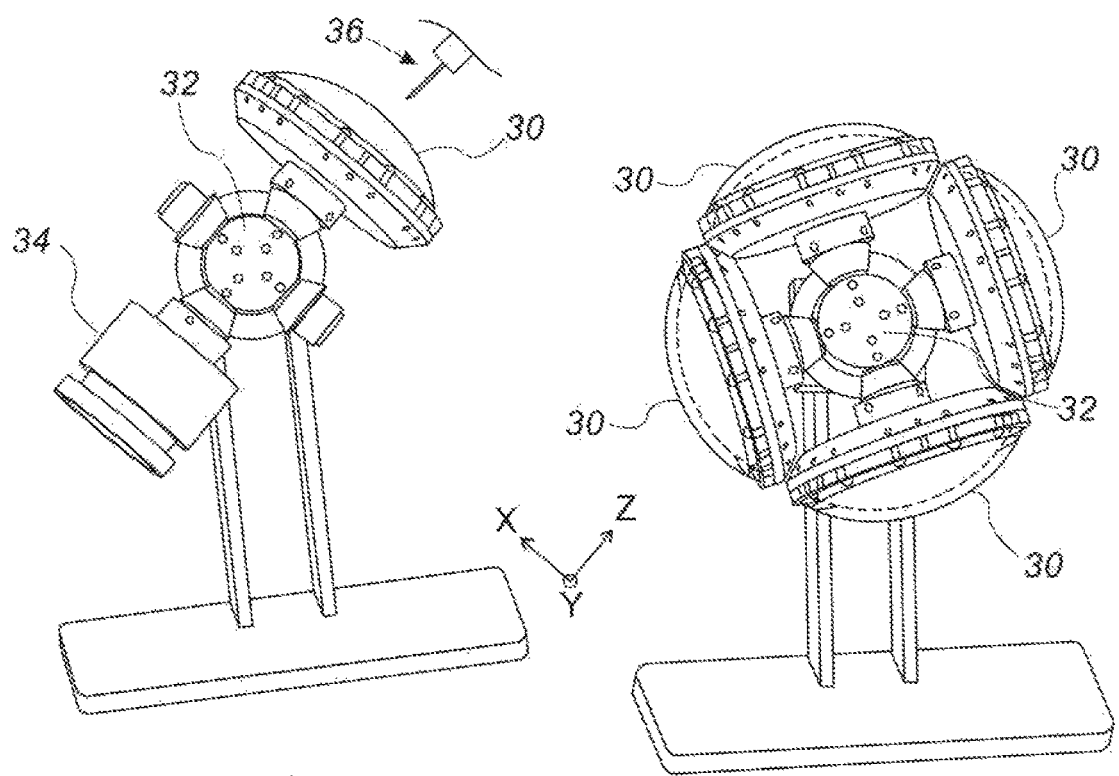
FIG. 2A
FIG. 2B

METHOD FOR PRODUCING SHELL AND FOAM FILLER FOR A BREAST IMPLANT

FIELD OF THE INVENTION

The present invention relates generally to medical implants, and particularly to breast implants.

BACKGROUND OF THE INVENTION

A breast implant is may be inserted in a human breast or attached on the breast, e.g., in order to replace tissue that has been medically removed in an operation such as a mastectomy, or for cosmetic purposes. The purpose of the breast implant is to restore the external form of the breast, including its tactile feel and weight.

Various technologies are employed to form breast implants. For example, U.S. Pat. No. 6,099,565 describes a biologically compatible human breast implant which has improved natural feel and is resistant to leakage. In the disclosed implant, a large quantity of small, pliable hollow spheroids of polymeric material are used as a filler within the implant shell. The hollow spheroids are partially filled with a fluid when in an uncompressed state and provide a cushioning effect by being compressible to the point where the resulting reduction in the interior space causes the interior to become essentially filled by the fluid and where further compression is resisted due to the relative non-compressibility of the contained fluid.

In another field, U.S. Patent Application Publication 2012/0303118 describes systems, devices, and methods for a prosthetic injectable intraocular lens. In an embodiment, the two parts of the lens body are fabricated by spin coating silicone elastomer on two molds. One mold corresponds to the anterior half of the lens; the other mold corresponds to the posterior half of the lens. After spin coating, the two halves are clamped and fused together and placed in a convection oven to cure. One or more silicone elastomeric patches located outside the optical path on the anterior side but away from the equator can be accessed by surgical needles in order to fill or adjust optically clear fluid within the lens. The elastomeric patches are sized so that they self-seal after a needle is withdrawn. A straight or stepped slit in the patch can allow a blunt needle to more easily access the interior of the lens.

SUMMARY OF THE INVENTION

An embodiment of the present invention provides a method for manufacturing a breast implant including producing a silicone shell of the breast implant by rotating a mold containing a silicone material to evenly spread the silicone material over an inner surface of the mold. Subsequently, an elastic filler material including silicone foam is formed in the shell by (i) injecting into the mold a mixture comprising silicone gel and gas bubbles and (ii) rotating the mold to homogenize the mixture.

In some embodiments, forming the elastic filler material includes injecting a hydrolyzed silicone mixed with carbonate and rotating the mold to homogenize a resulting mixture of silicone gel and carbon dioxide bubbles. In some embodiments, mixing the carbonate includes mixing sodium bicarbonate. In an embodiment, rotating the mold includes rotating the mold about three axes. In another embodiment, rotating the mold includes rotating the mold in a predefined sequence of rotations that specifies respective rotation axes and rotation speeds.

There is additionally provided, in accordance with an embodiment of the present invention, an apparatus for manufacturing breast implants, including one or more molds and a rotation mechanism. The one or more molds each have an internal volume shaped as a breast implant and are each configured to receive a first material for forming a silicone shell of the breast implant and subsequently receiving a second material for forming in the shell an elastic filler material comprising silicone foam. The rotation mechanism is configured to rotate the one or more molds so as to initially form the silicone shell and subsequently form the elastic filler material in each mold.

In some embodiments, one or more molds include multiple molds, and the rotation mechanism is configured to rotate the multiple molds simultaneously. In some embodiments, the apparatus further includes a counterbalance weight that is mounted on the rotation mechanism opposite one of the molds.

The present invention will be more fully understood from the following detailed description of the embodiments thereof, taken together with the drawings in which:

BRIEF DESCRIPTION OF THE DRAWINGS

FIG. 1 is a schematic sectional illustration of a human female breast with a breast implant, in accordance with an embodiment of the invention;

FIGS. 2A and 2B are schematic, pictorial illustrations of apparatuses for producing breast implants, in accordance with embodiments of the present invention.

DETAILED DESCRIPTION OF EMBODIMENTS

Overview

Figure 3:
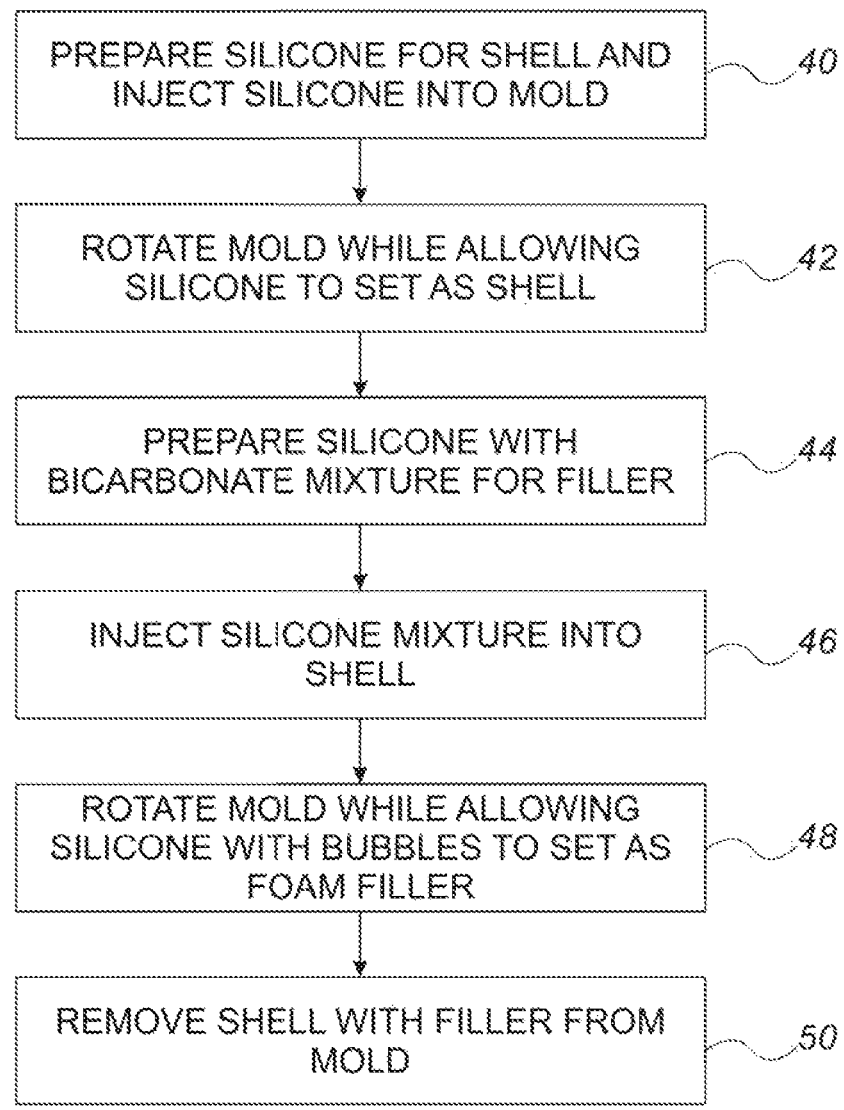
FIG. 3 is a flow chart that schematically illustrates a method for producing a breast implant, in accordance with an embodiment of the present invention.

A breast implant may contain an elastic filler material, such as silicone gel, which is contained in a sealed flexible shell. To form a light-weight implant, a gas such as air may be injected into the gel via the flexible shell, to effectively form a flexible and pliable foam. Producing a breast implant without, for example, compromising the shell integrity as air is being injected, is a time consuming and relatively laborious procedure.

Embodiments of the present invention that are described hereinafter provide apparatuses and methods for producing an implantable device that is used as a breast implant. The disclosed apparatuses are used both in producing a single integral silicone shell of the implant (i.e., a shell that is made-up of a single part, not assembled from two or more parts), and in producing the elastic filler for the shell.

In some embodiments, a method is applied for producing the silicone shell of the breast implant by rotating a mold containing a silicone material to evenly spread the silicone material over an inner surface of the mold, allowing the silicone material take the shape of the mold. subsequently, the disclosed method is applied to form in the shell an elastic filler material comprising silicone foam, by (i) injecting into the mold a mixture comprising silicone gel and gas bubbles and (ii) rotating the mold to homogenize the mixture.

In some embodiments, one or more molds are used, each having an internal volume shaped as a breast implant and each configured to receive a first material for forming a silicone shell of the breast implant and subsequently receiving a second material for forming in the shell an elastic filler material comprising silicone foam. The molds are mounted on a rotation mechanism, which is configured to rotate the one or more molds so as to initially form the silicone shell and subsequently form the elastic filler material in each mold.

In some embodiments, the elastic filler is produced inside the manufactured shell while it is still in the mold. In the process of producing the filler, the filled shell self-seals, so as to produce an implant made of the single integral shell, as further described below.

In some embodiments, the rotation mechanism of the disclosed apparatus is configured to rotate the one or more molds about three orthogonal axes, according to a preset sequence of directions and speeds of rotations. In a first step, silicone material for the shell is prepared (typically by mixing two precursors, i.e., compounds that participate in a chemical reaction that produces the silicone material for the shell) and the prepared silicone is injected into the mold. As noted above, when the mold is rotated, centrifugal forces cause the silicone to spread evenly over the inner surface of the mold where it sets, thereby receiving the final shape of the shell.

Once the shell has set in the mold, a silicone mixture for the filler material is prepared, for example, by adding sodium bicarbonate to mixed precursors. A non-limiting example method for chemically preparing a foam by adding sodium bicarbonate to hydrolyzed silicone monomer is described in U.S. Provisional Patent Application 62/658, 896, filed Apr. 17, 2018, entitled "Reducing Breast Implant Weight Using Chemically Produced Foam Filling," which is assigned to the assignee of the present patent application and whose disclosure is incorporated herein by reference.

The bicarbonate/silicone mixture is then injected into the shell. The mold is again rotated about three orthogonal axes, and the rotation now causes carbon dioxide bubbles, formed in the bicarbonate/silicone mixture, to be distributed uniformly throughout the mixture as it sets, thereby occupying the inside of the shell in a form of a homogenous foam filler. Once the foam filler has set, the complete implant may be removed from the mold.

In an embodiment, an apparatus comprising a single rotating mold is used for producing one implant at a time. In another embodiment, multiple (e.g., four) molds are mounted on the same rotation mechanism to produce multiple implants simultaneously, as described below. In an embodiment, the rotation mechanism is configured to rotate the multiple molds simultaneously.

The disclosed breast implant manufacturing apparatus and techniques can simplify the formation of light-weight breast implants, for example by eliminating manufacturing steps such as laborious shell sealing. Furthermore, the disclosed technique may simplify the manufacturing process of the elastic filler material itself (e.g., the silicone foam), by producing the foam inside the single integral shell from raw materials that are put inside the manufactured shell. The disclosed shell also has an improved sealing, thus reducing the likelihood of rupture or leakage in the subject's body after implantation. Thus, implementing the disclosed technique may increase the safety and the availability of light-weight breast implants.

Producing Integral Shell and Foam Filler for a Breast Implant

FIG. 1 is a schematic sectional illustration of a human female breast 20 with a breast implant 21, in accordance with an embodiment of the present invention. Implant 21 comprises a shell 22 filled with a light-weight foam 23, whereas the foam preparation is described in more detail below. In the disclosed embodiment, breast implant 21 is positioned as a sub-glandular implant between breast tissue 24 and a pectoralis major muscle 26. In alternative embodiments, breast implant 21 may be positioned either as a sub-fascial, sub-pectoral, or sub-muscular implant, referring to different positions of the implant relative to pectoralis major muscle 26, as will be understood by those skilled in the art. The example shown in FIG. 1 is thus chosen purely for the sake of conceptual clarity. Embodiments of the present invention may apply to any breast implant design that contains a foam.

FIGS. 2A and 2B are schematic, pictorial illustrations of apparatuses for producing breast implants, in accordance with embodiments of the present invention.

In the embodiment shown in FIG. 2A, the apparatus comprises a mold 30 and a counterbalance weight 34. The mold is shown after silicone gel has been injected for the shell via an inlet 36. A rotation mechanism 32 is configured to rotate mold 30 about three orthogonal axes, X, Y, and Z, so as to centrifugally force the silicone material for the shell inside mold 30 to evenly spread and set over the interior surface of mold 30. Mold 30 is similarly rotated after a silicone mixture, for an elastic filler, is injected into the mold, so as to centrifugally force the mixture to form a homogenous silicone foam filler.

In an embodiment, rotation mechanism 32 comprises one or more electrical motors and a transmission gear configured to rotate mold 30 as described above. In another embodiment, rotation mechanism 32 is connected to a controller (not shown) that instructs the rotation mechanism to perform a rotation sequence comprising directions and speeds of rotation.

In the embodiment shown in FIG. 2B, the apparatus comprises four molds 30 (e.g., two pairs of counterbalanced molds). The apparatus shown in FIG. 2B is thus capable of producing four implants simultaneously. In an embodiment, rotation mechanism 32 is configured to rotate the four molds simultaneously.

The apparatuses shown in FIGS. 2A and 2B are chosen purely for the sake of conceptual clarity. For example, machinery, such as piping for the injection of a mixture for the filler, is omitted for the simplicity of presentation. As another example, in an embodiment, the apparatuses comprise means to heat the molds to a preset temperature for a preset duration, so as to, for example, cure the foam filler.

FIG. 3 is a flow chart that schematically illustrates a method for producing a breast implant, in accordance with an embodiment of the present invention. The process begins with a user injecting into one or more molds 30 silicone material for producing a shell, at a silicon injection step 40. Next, at a shell manufacturing step 42, the user operates rotation mechanism 32 to rotate molds 30 to produce the implant shell as described above.

At a mixture preparation step 44, the user mixes silicone with sodium bicarbonate for the filler. The user then injects the silicone mixture into the manufactured single integral shell inside each mold 30, at a silicon mixture injection step 46. The user then operates rotation mechanism 32 to rotate molds 30 again, at a foam manufacturing step 48, to produce the implant filler comprising silicon with carbon dioxide bubbles, as described above. Finally, at a removal step 50, the user removes the filled shell (i.e., a complete breast implant) from each mold.

The flow chart shown in FIG. 3 is chosen purely for the sake of conceptual clarity. For example, the technique of producing foam using sodium bicarbonate is chosen by way of example. Alternatively, any other suitable techniques can be used. As another example, molds 30 may be mounted on rotation mechanism 32 in any other suitable geometry. Additional manufacturing steps, which may be used, are not shown for simplicity, e.g., a manufacturing step for curing in which the mold is heated.

Although the embodiments described herein mainly address breast implants, the methods and systems described herein can also be used in other applications, in which an implant comprising silicone-gel must be light-weight.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for manufacturing a breast implant, the method comprising:

producing a silicone shell of the breast implant by rotating a mold containing a silicone material to evenly spread the silicone material over an inner surface of the mold wherein said silicone material sets over said inner surface of the mold, thereby receiving a final shape of said silicone shell; and subsequently, once the silicone shell has set in the mold, forming in the shell an elastic filler material comprising silicone foam, by (i) injecting into the mold a mixture comprising silicone gel and sodium bicarbonate and (ii) rotating the mold to homogenize the mixture at a foam manufacturing step, causing forming carbon dioxide bubbles to be distributed uniformly throughout the mixture as it sets; wherein said silicone foam is formed inside said shell that is inside said mold, wherein said mold is heated to cure said silicone foam.

2. The method according to claim 1, wherein forming the elastic filler material comprises injecting a hydrolyzed silicone mixed with carbonate and rotating the mold to homogenize a resulting mixture of silicone gel and carbon dioxide bubbles.

3. The method according to claim 2, wherein mixing the carbonate comprises mixing sodium bicarbonate.

4. The method according to claim 1, wherein rotating the mold comprises rotating the mold about three axes.

5. The method according to claim 1, wherein rotating the mold comprises rotating the mold in a predefined sequence of rotations that specifies respective rotation axes and rotation speeds.

* * * * *